United States Patent
Rüdenauer

(10) Patent No.: US 8,993,812 B2
(45) Date of Patent: Mar. 31, 2015

(54) METHOD FOR PREPARING 2-METHYL-4-PHENYLBUTAN-2-OL

(71) Applicant: BASF SE, Ludwigshafen (DE)

(72) Inventor: Stefan Rüdenauer, Worms (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/018,544

(22) Filed: Sep. 5, 2013

(65) Prior Publication Data
US 2014/0073819 A1    Mar. 13, 2014

Related U.S. Application Data

(60) Provisional application No. 61/697,821, filed on Sep. 7, 2012.

(51) Int. Cl.
*C07C 33/18* (2006.01)
*C07C 29/36* (2006.01)

(52) U.S. Cl.
CPC ........................... *C07C 29/36* (2013.01)
USPC ........................... 568/715; 260/665 G

(58) Field of Classification Search
USPC ........................... 260/665 G; 568/715
See application file for complete search history.

(56) References Cited

U.S. PATENT DOCUMENTS

2006/0135400 A1    6/2006    Kuhn et al.

FOREIGN PATENT DOCUMENTS

| JP | 2000103754 A | 4/2000 |
| WO | WO-2004076393 A1 | 9/2004 |
| WO | WO-2011117360 A2 | 9/2011 |

OTHER PUBLICATIONS

Alam; Organic Process Research and Development; 2012, 16, 435-441; published on Feb. 16, 2012.*
Website; www.acros.com/_rainbow/pdf/ao_brochure-grignard.pdf, published on May 13, 2006, according to Wayback machine.*
Erdelyi et al., "Stereoselective production of (S)-1-aralkyl- and 1-arylethanols by freshly harvested and lyophilized yeast cells", Tetrahedron: Asymmetry 17, pp. 268-274, Jan. 23, 2006.
Norton et al., "The Action of Diethylmagnesium upon the Methyl Substituted Derivatives of Epoxy-ethane", *J. Am. Chem. Soc.*, 58 (11), pp. 2147-2150, Nov. 1, 1936.
International Search Report for PCT/EP2013/068432 dated Nov. 22, 2013.
Gaylord, N., et al., "The Reaction Between Grignard Reagents and the Oxirane Ring", Chemical Laboratories of the Polytechnic Institute of Brooklyn, Brooklyn, NY, Apr. 12, 1951.
English Translation of International Search Report for PCT/EP2013/068432, dated Nov. 22, 2013.

* cited by examiner

*Primary Examiner* — Sudhakar Katakam
*Assistant Examiner* — Pancham Bakshi
(74) *Attorney, Agent, or Firm* — Drinker Biddle & Reath LLP

(57) ABSTRACT

A method of preparing 2-methyl-4-phenylbutan-2-ol from a Grignard-type reaction of a benzylmagnesium halide with isobutylene oxide, and the use of the 2-methyl-4-phenylbutan-2-ol as a fragrance or flavoring, cosmetic agent, or detergent component.

14 Claims, No Drawings

METHOD FOR PREPARING 2-METHYL-4-PHENYLBUTAN-2-OL

CROSS-REFERENCE TO RELATED APPLICATIONS

This application claims benefit of U.S. Provisional Application Ser. No. 61/697,821, filed Sep. 7, 2012, which is incorporated herein by reference in its entirety.

BACKGROUND OF THE INVENTION

The present invention relates to a method for preparing 2-methyl-4-phenylbutan-2-ol.

2-Methyl-4-phenylbutan-2-ol, also referred to as dimethylphenylethylcarbinol or "muguet carbinol", is a fragrance with a floral aroma which is somewhat verdant and herbal, reminiscent of hyacinths and lilies (WO 2004/076393 A1). 2-Methyl-4-phenylbutan-2-ol is used for improving the aroma and/or flavour of a product or else to mask the innate aroma and/or flavour of a product. Furthermore, 2-methyl-4-phenylbutan-2-ol is a precursor in the preparation of other fragrances such as 4-cyclohexyl-2-methylbutan-2-ol, which is also referred to as coranol and has a scent of lily of the valley.

A method for preparing 4-cyclohexyl-2-methylbutan-2-ol in which 2-methyl-4-phenylbutan-2-ol is formed as an intermediate, has been described by Ebel et al. (WO 2011/117360). In this case, 2-methyl-4-phenylbutan-2-ol is formed by the reaction of styrene with isopropanol. A method for preparing dimethylphenylethylcarbinol by reacting methylmagnesium chloride with benzylacetone has been described by Yoichi et al. (JP 2000103754 A).

BRIEF SUMMARY OF THE INVENTION

The subject matter of the present invention is an alternative method for preparing 2-methyl-4-phenylbutan-2-ol from readily available starting materials. In this method, a benzylmagnesium halide is reacted with isobutylene oxide. The benzylmagnesium halide is preferably benzylmagnesium bromide or benzylmagnesium chloride, particularly benzylmagnesium bromide.

DETAILED DESCRIPTION OF THE INVENTION

The preparation of 2-methyl-4-phenylbutan-2-ol from a benzylmagnesium halide (I) and isobutylene oxide is shown in the following diagram, where X is a halogen, particularly chlorine, bromine or iodine, preferably bromine:

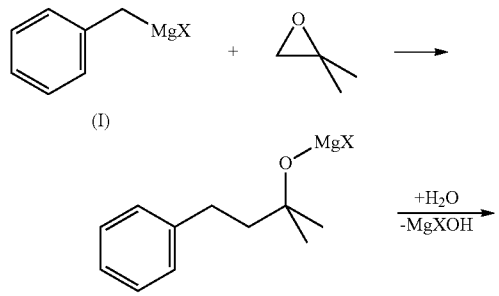

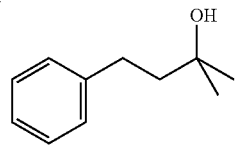

The benzylmagnesium halide (I) can be prepared in a known manner from magnesium and a benzyl halide (II).

The preparation of the benzylmagnesium halide (I) is shown in the following diagram, where X is a halogen, particularly chlorine, bromine or iodine, preferably bromine:

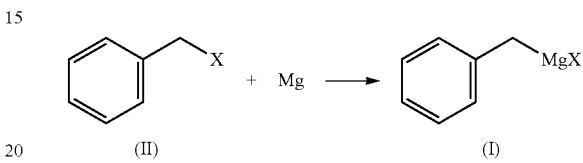

It is advantageous to use magnesium in stoichiometric excess, based on the benzyl halide (II). Preference is given to the use of 1 to 10 mol, preferably 1.5 to 5 mol, more preferably 2 to 3 mol and especially about 2.5 mol of magnesium per mole of benzyl halide.

Iodine may be added to activate the magnesium.

The reaction proceeds exothermically. The temperature of the reaction mixture is preferably kept between 0° C. and 70° C., particularly between 40° C. and 60° C. This may be achieved by, inter alia, appropriate adjustment of the addition rate of the benzyl halide (II) to the initial charge of magnesium.

The preparation of the benzylmagnesium halide (I) suitably takes place in a diluent in the absence of water. As diluent, the inert solvents mentioned below may be used.

The reaction of the benzylmagnesium halide (I) with isobutylene oxide may be carried out at various stoichiometric ratios of these starting materials. Benzylmagnesium halide (I) can be present in either stoichiometric excess or stoichiometric deficiency or in a stoichiometrically equivalent amount, with respect to the isobutylene oxide. Preference is given to using 0.5 to 5 mol, preferably 1.5 to 2.5 mol and especially 1 to 2 mol of benzylmagnesium halide per mole of isobutylene oxide.

Preference is given to adding the isobutylene oxide to an initial charge of the benzyl-magnesium halide (I). However, the benzylmagnesium halide (I) may also be added to an initial charge of the isobutylene oxide.

The reaction may be carried out either in a batchwise or semi-batchwise manner or else in a continuous mode.

The reaction of benzylmagnesium halide (I) with isobutylene oxide takes place conveniently in a diluent in the absence of water. Suitable diluents are solvents that are inert under the reaction conditions, in particular ethers, such as, for example, tetrahydrofuran, 2-methyltetrahydrofuran, 1,4-dioxane, diethyl ether, diisopropyl ether and/or dibutyl ether; aliphatic hydrocarbons, such as, for example, ligroin, heptane and/or octane; and aromatic hydrocarbons, such as, for example, benzene, toluene and/or xylene; and mixtures thereof. Preference is given to the use of an ether or ether mixture, particular preference to the use of tetrahydrofuran and/or 2-methyltetrahydrofuran. Preferably, the diluent is substantially anhydrous.

The reaction is carried out preferably in the presence of an epoxide ring-opening catalyst. Cu(I) compounds are preferred epoxide ring-opening catalysts. Suitable Cu(I) compounds are CuCl, CuBr, CuI and/or CuCN, among which preference is given to CuI. The Cu(I) compound is preferably used in amounts of 0.05 to 0.3 mol, of 0.07 to 0.15 mol and especially in an amount of approximately 0.1 mol per mole of isobutylene oxide. The Cu(I) compound is preferably added to the initial charge of benzylmagnesium halide. Subsequently the isobutylene oxide can be added.

The reaction of benzylmagnesium halide (I) with isobutylene oxide preferably takes place at −20° C. to +10° C., particularly at −10° C. to 0° C. This temperature can be attained by cooling the starting materials and/or the reaction vessel and also by appropriate adjustment of the rate with which the starting materials are combined. For this purpose, for instance, the addition rate of the isobutylene oxide to the initial charge of benzyl-magnesium halide can be adjusted; for example, a continuous addition of isobutylene oxide over a period of 0.5 to 1.5 hours can be carried out.

After the reaction has ended, workup of the reaction solution is carried out by hydrolysis, for example with water or else with aqueous acid or aqueous base. For aqueous acid workup, inorganic acids, such as, for example, hydrochloric acid or ammonium chloride, or else organic acids may be used. For workup with aqueous base, for example, aqueous solutions of sodium hydrogen carbonate, sodium carbonate, potassium hydrogen carbonate, potassium carbonate or sodium hydroxide may be used. The target product (the 2-methyl-4-phenylbutan-2-ol formed) can be separated by extraction from the aqueous phase and, after drying of the organic phase, be isolated therefrom by procedures such as distillation or melt crystallization.

One advantage of the method according to the invention is that the preparation of the benzylmagnesium halide (I) and its reaction with isobutylene oxide can be carried out without any intermediate operating steps in one reaction batch and in the same diluent. Accordingly, the present invention relates also to a method in which, as a first step, a benzyl halide (II) is reacted with magnesium as described, and the benzylmagnesium halide generated is subsequently reacted with isobutylene oxide in the presence of a Cu(I) compound as described.

The 2-methyl-4-phenylbutan-2-ol obtained by the method according to the invention may be used as a fragrance or flavouring, particularly in cosmetic agents, textile detergents and cleaning agents for hard surfaces.

Examples of such cosmetic agents comprise basically all cosmetic compositions, which typically comprise fragrances. These include, for example, eaux de parfum, eaux de toilette, eaux de cologne, aftershave products such as lotions and creams, pre-shave products, scented tissues, depilatory creams and lotions, tanning creams and lotions, hair care products such as shampoos, conditioners, setting lotions, hair gels, hair tinting agents, hair waxes, hair sprays, foam fixative compositions, hair mousses, split-end repair fluids, neutralizers for permanent waves, hair dyes and bleaches or "hot-oil-treatments", further, hand cleaning agents such as soaps, washing gels, shower gels, body care products such as creams, oils, lotions and the like for skin, in particular products for hand, face or foot care, sunscreens, deodorants and antiperspirants, skin antiseptics, insect repellents and decorative cosmetic products. Depending on the field of application, the cosmetic compositions may be formulated as an aqueous or alcoholic liquid, oil, (aerosol) spray, (aerosol) foam, mousse, gel, gel spray, cream, lotion, powder, tabs or waxes.

Washing detergents and cleaning agents, respectively, which can comprise the 2-methyl-4-phenylbutan-2-ol obtained by the method according to the invention include agents for cleaning and/or disinfection of surfaces, such as, for example, household cleaners, neutral cleaning agents, toilet cleaners, floor cleaners, carpet cleaners, window cleaners, polishes, furniture care products, liquid and solid dishwashing agents, liquid and solid automatic dishwasher detergents, further, agents for cleaning or treating textiles such as solid, semi-solid or liquid textile cleaning agents, laundry aftertreatment compositions, fabric softeners, ironing additives, textile fresheners, fabric preconditioning agents, washing soaps, washing tablets and the like.

Furthermore, the 2-methyl-4-phenylbutan-2-ol obtained by the method according to the invention may be used as a fragrant constitutent in other fragrance-containing products such as air purifiers, lamp oils, candles, indoor air fresheners, toilet blocks and the like.

The invention is further illustrated by means of the following examples:

EXAMPLE 1

Preparation of Benzylmagnesium Bromide

A 6 l reactor (HWS Labortechnik Mainz) with an outer heating mantle was inertized with argon. A suspension of 88.71 g of magnesium in 1500 ml tetrahydrofuran was placed in a flask and 0.50 g of iodine added with stirring. This resulted in a brownish-yellowish suspension. To this suspension were then added gradually 250.00 g of benzyl bromide over a period of 165 min using a dropping funnel. This rendered the solution colourless. After initial warming of the flask contents to 56° C. the reaction proceeded exothermically. The addition rate of the benzyl bromide was adjusted such that the temperature of the flask contents remained between 46° C. and 56° C. After completion of the addition of the benzyl bromide and cooling of the flask contents to room temperature, the supernatant was decanted into a second inertized flask.

EXAMPLE 2

Preparation of 2-methyl-4-phenylbutan-2-ol 13.92 g of copper(I) iodide were added to the supernatant obtained according to example 1, and the flask was cooled to −10° C. Then, 52.70 g of isobutylene oxide were added gradually over a period of 1 hour using a dropping funnel, and the temperature was maintained between −10° C. and −6° C. A mild exotherm was observed during this latter process. After stirring the mixture for a further 2 hours at 0° C., a sample was taken for analysis by gas chromatography. This sample was worked up with ammonium chloride solution. The reaction mixture was worked up by addition of 400 ml of saturated ammonium chloride solution, and 200 ml of toluene were added. The organic phase was separated off and washed twice with 400 ml each time of saturated ammonium chloride solution. After drying over magnesium sulfate, the product was obtained by distillation in vacuo with a purity of >97%. A total of 88.9 g of 2-methyl-4-phenylbutan-2-ol were obtained, corresponding to a yield of 74%.

The invention claimed is:
1. A method for preparing 2-methyl-4-phenylbutan-2-ol, said method comprising reacting a benzylmagnesium halide with isobutylene oxide, wherein 0.5 to 5 mol of benzylmagnesium halide is used per mole of isobutylene oxide.

2. The method of claim 1, wherein the benzylmagnesium halide is benzylmagnesium bromide or benzylmagnesium chloride.

3. The method of claim 1, wherein the reaction is carried out in the presence of at least one Cu(I) compound.

4. The method of claim 3, wherein the Cu(I) compound is copper(I) iodide.

5. The method of claim 3, wherein 0.05 to 0.3 mol of the Cu(I) compound is used per mole of isobutylene oxide.

6. The method of claim 1, wherein the benzylmagnesium halide is obtained by reaction of a benzyl halide with magnesium.

7. The method of claim 6, wherein 1 to 10 mol of magnesium is used per mole of benzyl halide.

8. The method of claim 6, wherein the reaction of the benzyl halide with magnesium and the reaction of the thus formed benzylmagnesium halide with isobutylene oxide take place in the same diluent.

9. The method of claim 8, wherein the diluent is an ether.

10. The method of claim 9, wherein the ether is tetrahydrofuran or 2-methyltetrahydrofuran.

11. The method of claim 6, wherein the reaction of the formed benzylmagnesium halide with the isobutylene oxide is conducted in a reaction mixture maintained at a temperature range of −20° C. to 10° C.

12. The method of claim 8, wherein the reaction of the benzyl halide with magnesium and the reaction of the thus formed benzylmagnesium halide with isobutylene oxide is conducted in one reaction batch in which, in one step, the benzyl halide is reacted with the magnesium, and in a subsequent step, the formed benzylmagnesium halide is reacted with the isobutylene oxide.

13. The method of claim 12, wherein the reaction of the benzylmagnesium halide with the isobutylene oxide is carried out in the presence of at least one Cu(I) compound.

14. The method of claim 13, wherein the 2-methyl-4-phenylbutan-2-ol, following an aqueous work-up and vacuum distillation, has a purity of at least 97%.

\* \* \* \* \*